(12) United States Patent
Axelrod et al.

(10) Patent No.: US 10,364,204 B2
(45) Date of Patent: Jul. 30, 2019

(54) PROCESS FOR MANUFACTURING METHYL TERTIARY-BUTYL ETHER (MTBE) AND OTHER HYDROCARBONS

(71) Applicant: Lyondell Chemical Technology, L.P., Houston, TX (US)

(72) Inventors: Michael G. Axelrod, Newtown Square, PA (US); Steven T. Coleman, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/173,042

(22) Filed: Jun. 3, 2016

(65) Prior Publication Data

US 2016/0368848 A1 Dec. 22, 2016

Related U.S. Application Data (60) Provisional application No. 62/183,014, filed on Jun. 22, 2015.

(51) Int. Cl.

| | | |
|---|---|---|
| *C07C 41/06* | (2006.01) | |
| *C07C 4/02* | (2006.01) | |
| *C07C 2/56* | (2006.01) | |
| *C07C 5/25* | (2006.01) | |
| *C07C 29/50* | (2006.01) | |
| *C07C 5/327* | (2006.01) | |
| *C07C 2/36* | (2006.01) | |
| *C07C 2/22* | (2006.01) | |
| *C07C 4/04* | (2006.01) | |
| *C07C 5/27* | (2006.01) | |
| *C07C 29/151* | (2006.01) | |
| *C10L 1/06* | (2006.01) | |

(52) U.S. Cl.
CPC ............. *C07C 41/06* (2013.01); *C07C 2/22* (2013.01); *C07C 4/04* (2013.01); *C07C 5/2775* (2013.01); *C07C 29/1518* (2013.01); *C10L 1/06* (2013.01); *C07C 2529/65* (2013.01); *C07C 2531/14* (2013.01); *C07C 2531/24* (2013.01); *Y02P 20/52* (2015.11)

(58) Field of Classification Search
None
See application file for complete search history.

(56) References Cited

U.S. PATENT DOCUMENTS

| | | | | |
|---|---|---|---|---|
| 3,321,546 A | * | 5/1967 | Roest | B01J 31/0212 |
| | | | | 502/117 |
| 4,504,688 A | * | 3/1985 | Herwig | C07C 7/14891 |
| | | | | 568/697 |
| 4,760,210 A | * | 7/1988 | Sweeney | B01J 8/0285 |
| | | | | 165/8 |
| 5,260,499 A | | 11/1993 | Wu | |
| 5,659,090 A | * | 8/1997 | Cameron | C07C 41/01 |
| | | | | 568/671 |
| 5,689,015 A | | 11/1997 | Hunt et al. | |
| 5,990,370 A | | 11/1999 | Sims | |
| 6,323,384 B1 | | 11/2001 | Powers et al. | |
| 8,395,005 B2 | * | 3/2013 | Coleman | C07C 2/36 |
| | | | | 585/324 |

FOREIGN PATENT DOCUMENTS

| | | |
|---|---|---|
| EP | 905110 A2 | 3/1999 |
| WO | WO-9732901 A1 | 9/1997 |

OTHER PUBLICATIONS

Guisnet et al. ("Skeletal Isomerization of n-Butenes", Journal of Catalysis, vol. 158, 1996, pp. 551-560).*
International Search Report and Written Opinion for PCT/US2016/038558 dated Sep. 23, 2016.

\* cited by examiner

*Primary Examiner* — Rosalynd A Keys (57) ABSTRACT

A process for manufacturing methyl t-butyl ether (MTBE) including (A) an optional first step including cracking raw material made from or containing ethane and/or propane, to form ethylene and recovering the residual uncracked raw material, (B) a second step including dimerizing ethylene to form n-butylene, (C) a third step including isomerizing the n-butylene to form isobutylene, (D) an optional fourth step including oxidizing methane to form methanol, (E) a fifth step including etherifying the isobutylene with methanol to form methyl t-butyl ether, and (F) a sixth step including collecting the methyl t-butyl ether is provided. The process can also be used to prepare gasoline alkylate, a higher molecular weight ethylene oligomer, a higher-molecular-weight-ethylene-oligomer-based methyl ether, an isomerized higher molecular weight ethylene oligomer, or an isomerized-higher-molecular-weight-ethylene-oligomer-based methyl ether.

9 Claims, 2 Drawing Sheets

PROCESS FOR MANUFACTURING METHYL TERTIARY-BUTYL ETHER (MTBE) AND OTHER HYDROCARBONS

CROSS-REFERENCE TO RELATED APPLICATIONS

This application claims benefit of priority to U.S. Provisional Application No. 62/183,014 filed on Jun. 22, 2015, which is incorporated herein by reference in its entirety.

FIELD OF THE INVENTION

In general, the present disclosure relates to the field of chemistry. More specifically, the present disclosure relates to a process for manufacturing methyl tertiary-butyl ether (MTBE) and other hydrocarbons. In particular, the present disclosure relates to a process for manufacturing MTBE, other gasoline blend stocks and hydrocarbons from methanol and ethylene.

BACKGROUND OF THE INVENTION

Methyl t-butyl ether (MTBE) is a useful additive for gasoline. It is an alternative to lead, has a high octane number, and is miscible with gasoline. MTBE can be manufactured by the etherification of isobutylene with methanol.

Alkylates are valued gasoline blend stocks due to their high octane, low vapor pressure and low sulfur content. They may be produced by reacting isobutane with a $C_3$-$C_5$ olefin in the presence of a strong acid catalyst to produce a $C_7$-$C_9$ isoparaffinic stream that is often referred to as an alkylate stream. Both of these high value gasoline blend stocks may be produced from a $C_4$ olefin feedstock.

There is a need to manufacture MTBE and additional gasoline blend stocks from other feedstocks.

SUMMARY OF THE INVENTION

The present disclosure relates to a process for producing MTBE and gasoline alkylates wherein olefins such as ethylene may provide the necessary and cost effective olefinic feed component for the production of MTBE and/or gasoline alkylate. In some embodiments, the present disclosure provides a process for manufacturing methyl t-butyl ether including (A) an optional first step including (i) cracking raw material made from or containing ethane and/or propane, to form ethylene and (ii) recovering residual uncracked raw material, (B) a second step including (i) dimerizing ethylene to form n-butylene, (C) a third step including (i) isomerizing the n-butylene to form isobutylene, (D) an optional fourth step including (i) oxidizing methane to form methanol, (E) a fifth step including (i) etherifying the isobutylene with methanol to form methyl t-butyl ether, and (F) a sixth step including (i) collecting methyl t-butyl ether. In further embodiments, the raw material has previously been processed or "cracked" such that a sufficient concentration of ethylene is present for being dimerized and forming n-butylene.

In some embodiments, the present disclosure provides a process for manufacturing methyl t-butyl ether wherein the second step further includes (ii) recovering unconverted ethylene, (iii) alkylating n-butylene with isobutane to form gasoline alkylate, and (iv) recovering gasoline alkylate.

In additional embodiments, the present disclosure provides a process for manufacturing methyl t-butyl ether wherein the second step further includes (ii) recovering unconverted ethylene, (v) dimerizing combinations of at least three ethylene molecules to form a higher molecular weight ethylene oligomer, and (vi) recovering the higher molecular weight ethylene oligomer. In further embodiments, the present disclosure provides a process for manufacturing methyl t-butyl ether wherein the fifth step further includes (ii) etherifying the higher molecular weight ethylene oligomer with methanol to form a higher-molecular-weight-ethylene-oligomer-based methyl ether and (iii) recovering the higher-molecular-weight-ethylene-oligomer-based methyl ether.

In some embodiments, the present disclosure provides a process for manufacturing methyl t-butyl ether wherein the third step further includes (ii) recovering unconverted n-butylene, (iii) alkylating isobutylene with isobutane to form gasoline alkylate, and (iv) recovering gasoline alkylate.

In further embodiments, the present disclosure provides a process for manufacturing methyl t-butyl ether wherein the third step further includes (ii) recovering unconverted n-butylene, (v) isomerizing a higher molecular weight ethylene oligomer, and (vi) recovering the isomerized higher molecular weight ethylene oligomer. In some embodiments, the present disclosure provides a process for manufacturing methyl t-butyl ether wherein the fifth step further includes (ii) etherifying an isomerized higher molecular weight ethylene oligomer with methanol to form an isomerized-higher-molecular-weight-ethylene-oligomer-based methyl ether and (iii) recovering the isomerized-higher-molecular-weight-ethylene-oligomer-based methyl ether.

In some embodiments, the present disclosure provides a process for manufacturing methyl t-butyl ether wherein the optional fourth step further includes (ii) recovering unconverted methane.

In a general embodiment, the present disclosure provides a process for manufacturing methyl t-butyl ether including (A) an optional first step including (i) cracking raw material made from or containing ethane and/or propane, to form ethylene and (ii) recovering residual uncracked raw material, (B) a second step including (i) dimerizing ethylene to form n-butylene, (ii) recovering unconverted ethylene, (iii) alkylating n-butylene with isobutane to form gasoline alkylate, (iv) recovering gasoline alkylate, (v) dimerizing combinations of at least three ethylene molecules to form a higher molecular weight ethylene oligomer, and (vi) recovering the higher molecular weight ethylene oligomer, (C) a third step including (i) isomerizing the n-butylene to form isobutylene, (ii) recovering unconverted n-butylene, (iii) alkylating isobutylene with isobutane to form gasoline alkylate, (iv) recovering gasoline alkylate, (v) isomerizing a higher molecular weight ethylene oligomer, and (vi) recovering the isomerized higher molecular weight ethylene oligomer, (D) an optional fourth step including (i) oxidizing methane to form methanol and (ii) recovering unconverted methane, (E) a fifth step including (i) etherifying the isobutylene with methanol to form methyl t-butyl ether, (ii) etherifying a higher molecular weight ethylene oligomer with methanol to form a higher-molecular-weight-ethylene-oligomer-based methyl ether, (iii) recovering the higher-molecular-weight-ethylene-oligomer-based methyl ether, (iv) etherifying an isomerized higher molecular weight ethylene oligomer with methanol to form an isomerized-higher-molecular-weight-ethylene-oligomer-based methyl ether, and (v) recovering the isomerized-higher-molecular-weight-ethylene-oligomer-based methyl ether, and (F) a sixth step including (i) collecting methyl t-butyl ether.

In a general embodiment, the present disclosure provides for the production of methyl t-butyl ether prepared by a process including (A) an optional first step including (i) cracking raw material made from or containing ethane and/or propane, to form ethylene and (ii) recovering residual uncracked raw material, (B) a second step including (i) dimerizing ethylene to form n-butylene, (C) a third step including (i) isomerizing the n-butylene to form isobutylene, (D) an optional fourth step including (i) oxidizing methane to form methanol, (E) a fifth step including (i) etherifying the isobutylene with methanol to form methyl t-butyl ether, and (F) a sixth step including (i) collecting methyl t-butyl ether.

In particular embodiments, the present disclosure provides a method for preparing methyl t-butyl ether, gasoline alkylate, a higher molecular weight ethylene oligomer, a higher-molecular-weight-ethylene-oligomer-based methyl ether, an isomerized higher molecular weight ethylene oligomer or an isomerized-higher-molecular-weight-ethylene-oligomer-based methyl ether.

In some embodiments, the present disclosure provides a method for the preparation of gasoline alkylate cracking raw material comprising ethane or propane to form ethylene; dimerizing ethylene to form n-butylene; isomerizing the n-butylene to form isobutylene; alkylating n-butylene with isobutane to form gasoline alkylate, and recovering gasoline alkylate. In further embodiments, the method for preparing gasoline alkylate cracking raw material comprises recovering residual uncracked raw material that may be, in certain embodiments, further processed to produce ethylene for the production of gasoline alkylate and/or MTBE.

In some embodiments, the present disclosure relates to a process for manufacturing methyl t-butyl ether comprising: a first step comprising dimerizing ethylene to form n-butylene; a second step comprising isomerizing the n-butylene to form isobutylene using an isomerization reactor; and a third step comprising etherifying the isobutylene with methanol to form methyl t-butyl ether and recycling the unreacted normal butenes to the isomerization reactor.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

BRIEF DESCRIPTION OF THE DRAWINGS

The following figures illustrate preferred embodiments of the subject matter disclosed herein. The claimed subject matter may be understood by reference to the following description taken in conjunction with the accompanying figures, in which like reference numerals identify like elements, and in which:

DETAILED DESCRIPTION OF THE INVENTION

The present technology is described more fully hereinafter. However, this technology can be embodied in many different forms and should not be construed as limited to the embodiments set forth herein; rather, these embodiments are provided so that this disclosure will satisfy applicable legal requirements. As such, it will be apparent to those skilled in the art that the embodiments can incorporate changes and modifications without departing from the general scope. It is intended to include all the modifications and alterations in so far as the modifications and alterations come within the scope of the appended claims or the equivalents thereof.

As used in this specification and the claims, the singular forms "a," "an," and "the" include plural referents unless the context clearly dictates otherwise.

As used in this specification and the claims, the terms "comprising," "containing," or "including" mean that at least the named compound, element, material, particle, or method step, etc., is present in the composition, the article, or the method, but does not exclude the presence of other compounds, elements, materials, particles, or method steps, etc., even if the other such compounds, elements, materials, particles, or method steps, etc., have the same function as that which is named, unless expressly excluded in the claims. It is also to be understood that the mention of one or more method steps does not preclude the presence of additional method steps before or after the combined recited steps or intervening method steps between those steps expressly identified.

Moreover, it is also to be understood that the lettering of process steps or ingredients is a means for identifying discrete activities or ingredients and the recited lettering can be arranged in any sequence, unless expressly indicated.

For the purpose of the present description and of the claims which follow, except where otherwise indicated, numbers expressing amounts, quantities, percentages, and so forth, are to be understood as being modified by the term "about". Also, ranges include any combination of the maximum and minimum points disclosed and include any intermediate ranges therein, which may or may not be specifically enumerated herein.

Definitions

In the present description, the terms "alkylating" or "alkylation" refers to the transfer of an alkyl group from one molecule to another, such as the combining of $C_3$-$C_5$ olefins with isobutane in the presence of a strong acid catalyst.

In the present description, the term "cracking" refers to the breaking down of hydrocarbons into smaller alkanes and alkenes by using heat, pressure, catalysts, or combinations thereof.

In the present description, the terms "dimerizing" or "dimerization" refer to the bonding of two identical molecular subunits to form a single dimer. The bonding may be covalent or intermolecular, e.g. hydrogen bonding.

In the present description, the terms "etherifying" or "etherification" refer to the conversion of an alcohol to an ether in the presence of an acid, an etherification catalyst or via the Williamson ether synthesis.

In the present description, the term "first" refers to the order in which a particular step is presented and does not necessarily indicate that a "second" step will be presented. For example, "first step" refers to the first of at least one process step. The term does not reflect priority, importance, or significance in any other way. Similar terms used that can be used herein include "second," "third," "fourth," etc.

In the present description, the term "gasoline alkylate" refers to a combination of olefins which are formed by alkylation of n-butylene or iso-butylene with isobutane.

In the present description, the term "higher molecular weight ethylene oligomer" refers to a combination of olefins having a molecular weight greater than n-butylene (e.g., hexene, octene, etc.), which are formed by dimerization of three or more ethylene molecules.

In the present description, the term "isomerizing" refers to the chemical process under which a compound is transformed into any of its isomeric forms, (i.e., compounds with the same chemical composition but with different structures or configurations).

In the present description, the term "n-butylene" refers to all forms of n-butylene, for example, 1-butene and 2-butene, trans-2-butene or cis-2-butene, and mixtures thereof.

In a general embodiment, the present disclosure provides a process for manufacturing methyl t-butyl ether including a first step including cracking raw material made from or containing ethane and/or propane, to form ethylene, and recovering the residual uncracked raw material; a second step including dimerizing ethylene to form n-butylene (and higher molecular weight ethylene oligomers); a third step including isomerizing the n-butylene to form isobutylene; an optional fourth step including oxidizing methane to form methanol; a fifth step including etherifying the isobutylene with methanol to form methyl t-butyl ether; and a sixth step including collecting methyl t-butyl ether.

The optional first step includes (i) cracking raw material made from or containing ethane and/or propane to form ethylene and (ii) recovering the residual uncracked raw material. Steam cracking of hydrocarbon feedstocks produces ethylene, propylene, butenes (1-butene, isobutene, cis-2-butene, and trans-2-butene and mixtures thereof), butadiene, isoprene, aromatics, gasoline components, etc., and combinations thereof. The relative proportions of ethylene and propylene produced in a steam cracking operation can be modulated by changing the nature of the feedstock and by modifying the operating conditions of the cracking process.

In an olefin plant, a hydrocarbon feedstock such as naphtha, gas oil, or other fractions of whole crude oil may be mixed with steam. This mixture, after preheating, is often subjected to severe thermal cracking at elevated temperatures in a pyrolysis furnace. The cracked effluent from the pyrolysis furnace contains variable, gaseous hydrocarbons (from 1 to 35 carbon atoms per molecule). This effluent contains hydrocarbons that are aliphatic, aromatic, saturated, and unsaturated, and may contain significant amounts of molecular hydrogen. The cracked product of a pyrolysis furnace is then further processed in the olefin plant to produce various individual product streams such as hydrogen, ethylene, propylene, mixed hydrocarbons having four or five carbon atoms per molecule, and pyrolysis gasoline.

In some embodiments, the second step of the process includes (i) dimerizing ethylene to form n-butylene. The dimerization catalyst can be a homogeneous catalyst or a heterogeneous catalyst. Examples of suitable homogeneous catalysts are taught in U.S. Pat. Nos. 3,321,546; 4,242,531; 4,476,341; 5,260,499 and 5,414,178; the teachings of which are herein incorporated by reference.

In certain embodiments, the dimerization catalyst comprises a nickel compound and an organo aluminium compound. Suitable nickel compounds include nickel salts of a mono- or dicarboxylic acid, such as nickel oleate, nickel dodecanoate, and nickel octanoate. Other nickel compounds include coordination complexes of organic phosphines with nickel salts. Examples of such complexes are nickel bis(triethylphosphine) chloride [Ni(Et$_3$P)$_2$Cl$_2$], nickel bis(triphenylphosphine) octanoate, nickel bis(tributylphosphine) chloride, and nickel bis(tricyclohexylphosphine) chloride.

Suitable organo aluminium compounds include those having 1 to 2 alkyl groups and 1 to 2 halogen atoms per aluminium atom. In certain embodiments, the alkyl groups have 1 to 5 carbon atoms.

One dimerization catalyst is made from or contains nickel bis(triphenylphosphine) octanoate and ethyl aluminium dichloride. The molar ratio Ni:Al can be, in some embodiments, from 0.9:10 to 1:2.5, from 09:8 to 1:5, and from 1:2.5 to 1:4.

The dimerization reaction is typically performed at a temperature within a range of from about 10 degrees Celsius to about 100 degrees Celsius (10-100° C.), such as from 50-75° C. The dimerization reaction can be carried out in a liquid or gas phase by contacting ethylene with the catalyst, depending on the reaction temperature and pressure employed. The pressure of the dimerization reaction can be from about 345 kPa to about 13,790 kPa, including from about 500-10,000 kPa.

The dimerization reaction produces a dimerization mixture that comprises ethylene, 1-butene, and 2-butenes. Other olefins such as hexenes and octenes may be present in the dimerization mixture. In certain embodiments, the amount of hexenes, octenes, and other higher olefins produced can be adjusted, e.g. minimized, by selecting an appropriate catalyst and controlling ethylene conversion. Higher butenes selectivities can be achieved by running at lower ethylene conversions.

The third step includes (i) isomerizing the n-butylene to form isobutylene. Many isomerization catalysts can be used. Suitable acidic catalysts include acidic ion-exchange resins such as sulfonated resins (see, e.g., U.S. Pat. No. 3,326,866, the teachings of which are incorporated herein by reference), organosulfonic acids, phosphoric acid, carboxylic acids, metal oxides (alumina, zirconia, sulfated zirconia), mixed oxides (e.g., silica-alumina, zirconia-silica), acidic zeolites, acidic clays (see, e.g., U.S. Pat. Nos. 6,323,384 and 4,992,613; U.S. Patent Application Publication Nos. 2004/0249229 and 2006/0084831, the teachings of which are incorporated herein by reference).

When an acidic catalyst is used, the isomerization can be conducted at a temperature from about 40 degrees Celsius to about 200 degrees Celsius (40-200° C.), such as from 100-150° C., and under a pressure of about 345 kPa to about 3450 kPa, including from about 500-10,000 kPa. In some embodiments, the weight hourly space velocities (WHSV) are maintained at about 0.2 kg feed per kg catalyst per hour to about 4 kg feed per kg catalyst per hour, and from 1 kg feed per kg of catalyst per hour to about 3 kg feed per kg catalyst per hour.

The basic isomerization catalysts can be metal oxides such as magnesium oxide, calcium oxide, barium oxide, and lithium oxide. In certain embodiments, metal oxides supported on a carrier may be used. Examples of carriers include silica, alumina, titania, silica/alumina, and mixtures thereof.

The isomerization catalysts can be present as beads, granules, pellets, extrudates, tablets, agglomerates, and combinations thereof.

In some embodiments, an optional fourth step includes (i) oxidizing methane to form methanol. First, methane gas can be converted into a synthesis gas stream consisting of CO, $CO_2$, $H_2O$ and hydrogen, by the catalytic reforming of methane gas and steam or by partial oxidation. Next, the synthesis gas is catalytically synthesized into methanol.

In further embodiments, the fifth step includes (i) etherifying the isobutylene with methanol to form methyl t-butyl ether. The methanol and the isobutylene can be reacted in the liquid phase over a solid phase strong acid ion-exchange resin catalyst to produce methyl t-butyl ether (MTBE).

In certain embodiments, a mixture of excess methanol and methyl t-butyl ether can be withdrawn from the etherification reactor and then distilled to give a methanol/methyl t-butyl ether azeotrope, which may be recycled to the etherification reactor. The methyl t-butyl ether can be collected and further purified by distillation.

In some embodiments, the present disclosure provides a process for manufacturing methyl t-butyl ether wherein (B) the second step further includes (ii) recovering unconverted ethylene; (iii) alkylating n-butylene with isobutane to form gasoline alkylate, and (iv) recovering gasoline alkylate.

The alkylation of n-butylene (or isobutylene) with isobutane to form gasoline alkylate can be achieved with an alkylation catalyst. Examples of alkylation catalysts include hydrofluoric acid, sulfuric acid, phosphoric acid, and metal halides. Furthermore, the catalyst can contain various additives or promoters such as boron trifluoride.

The alkylation reaction can be carried out with a substantial molar excess of isobutane. In some embodiments, the system operates at a catalyst:hydrocarbon volume ratio of 1:1 to 4:1, and from 1:1 to 3:1.

The pressure in the reactors has to be at least high enough to keep the n-butylene in the liquid phase for conducting the alkylation reaction. In some embodiments, the minimum pressure is about 600 kPa, and the temperature range is about 15 degrees Celsius to about 50 degrees Celsius (15-50° C.) and from about 25-40° C.

Alternatively, the alkylation can be achieved by an ionic liquid catalyzed process, wherein at least one hydrocarbon stream is contacted with an ionic liquid catalyst as described, e.g. in U.S. Pat. No. 7,432,408 and U.S. Patent Application Publication No. 2013/0066130, the teachings of which are incorporated herein by reference.

In additional embodiments, the present disclosure provides a process for manufacturing methyl t-butyl ether, wherein (B) the second step further includes (iv) recovering unconverted ethylene; (v) dimerizing combinations of at least three ethylene molecules to a form higher molecular weight ethylene oligomer; and (vi) recovering the higher molecular weight ethylene oligomer.

In certain embodiments, the present disclosure provides a process for manufacturing methyl t-butyl ether, wherein (E), the fifth step, further includes: (ii) etherifying a higher molecular weight ethylene oligomer with methanol to form a higher-molecular-weight-ethylene-oligomer-based methyl ether; and (iii) recovering the higher-molecular-weight-ethylene-oligomer-based methyl ether.

In some embodiments, the present disclosure provides a process for manufacturing methyl t-butyl ether wherein (C), the third step, further includes (ii) recovering unconverted n-butylene; (iii) alkylating isobutylene with isobutane to form gasoline alkylate; and (iv) recovering the gasoline alkylate.

In some embodiments, the present disclosure provides a process for manufacturing methyl t-butyl ether, wherein (C), the third step further includes (ii) recovering unconverted n-butylene; (v) isomerizing a higher molecular weight ethylene oligomer; and (vi) recovering the isomerized higher molecular weight ethylene oligomer.

In further embodiments, the present disclosure provides a process for manufacturing methyl t-butyl ether wherein (E), the fifth step, further includes: (ii) etherifying a higher molecular weight ethylene oligomer with methanol to form a higher-molecular-weight-ethylene-oligomer-based methyl ether; (iii) recovering the higher-molecular-weight-ethylene-oligomer-based methyl ether; (iv) etherifying an isomerized higher molecular weight ethylene oligomer with methanol to form an isomerized-higher-molecular-weight-ethylene-oligomer-based methyl ether; and (v) recovering the isomerized-higher-molecular-weight-ethylene-oligomer-based methyl ether.

In some embodiments, the present disclosure provides a process for manufacturing methyl t-butyl ether wherein (D), the optional fourth step, further includes (ii) recovering unconverted methane.

In a general embodiment, the present disclosure provides a process for manufacturing methyl t-butyl ether including (A) an optional first step including (i) cracking raw material made from or containing ethane and/or propane to form ethylene; and (ii) recovering residual uncracked raw material; (B) a second step including (i) dimerizing ethylene to form n-butylene; (ii) recovering unconverted ethylene; (iii) alkylating n-butylene with isobutane to form gasoline alkylate; (iv) recovering gasoline alkylate; (v) dimerizing combinations of at least three ethylene molecules to form higher molecular weight ethylene oligomer; and (vi) recovering higher molecular weight ethylene oligomer; (C) a third step including (i) isomerizing the n-butylene to form isobutylene; (ii) recovering unconverted n-butylene; (iii) alkylating isobutylene with isobutane to form gasoline alkylate; and (iv) recovering gasoline alkylate; (v) isomerizing a higher molecular weight ethylene oligomer; and (vi) recovering the isomerized higher molecular weight ethylene oligomer; (D) an optional fourth step including (i) oxidizing ethane to form methanol; and (ii) recovering unconverted methane; (E) a fifth step including (i)etherifying the isobutylene with methanol to form methyl t-butyl ether; (ii) etherifying a higher molecular weight ethylene oligomer with methanol to form a higher-molecular-weight-ethylene-oligomer-based methyl ether; (iii) recovering the higher-molecular-weight-ethylene-oligomer-based methyl ether; (iv) etherifying an isomerized higher molecular weight ethylene oligomer with methanol to form an isomerized-higher-molecular-weight-ethylene-oligomer-based methyl ether; and (v) recovering the isomerized-higher-molecular-weight-ethylene-oligomer-based methyl ether; and (F) a sixth step including (i) collecting methyl t-butyl ether.

Figure 1:
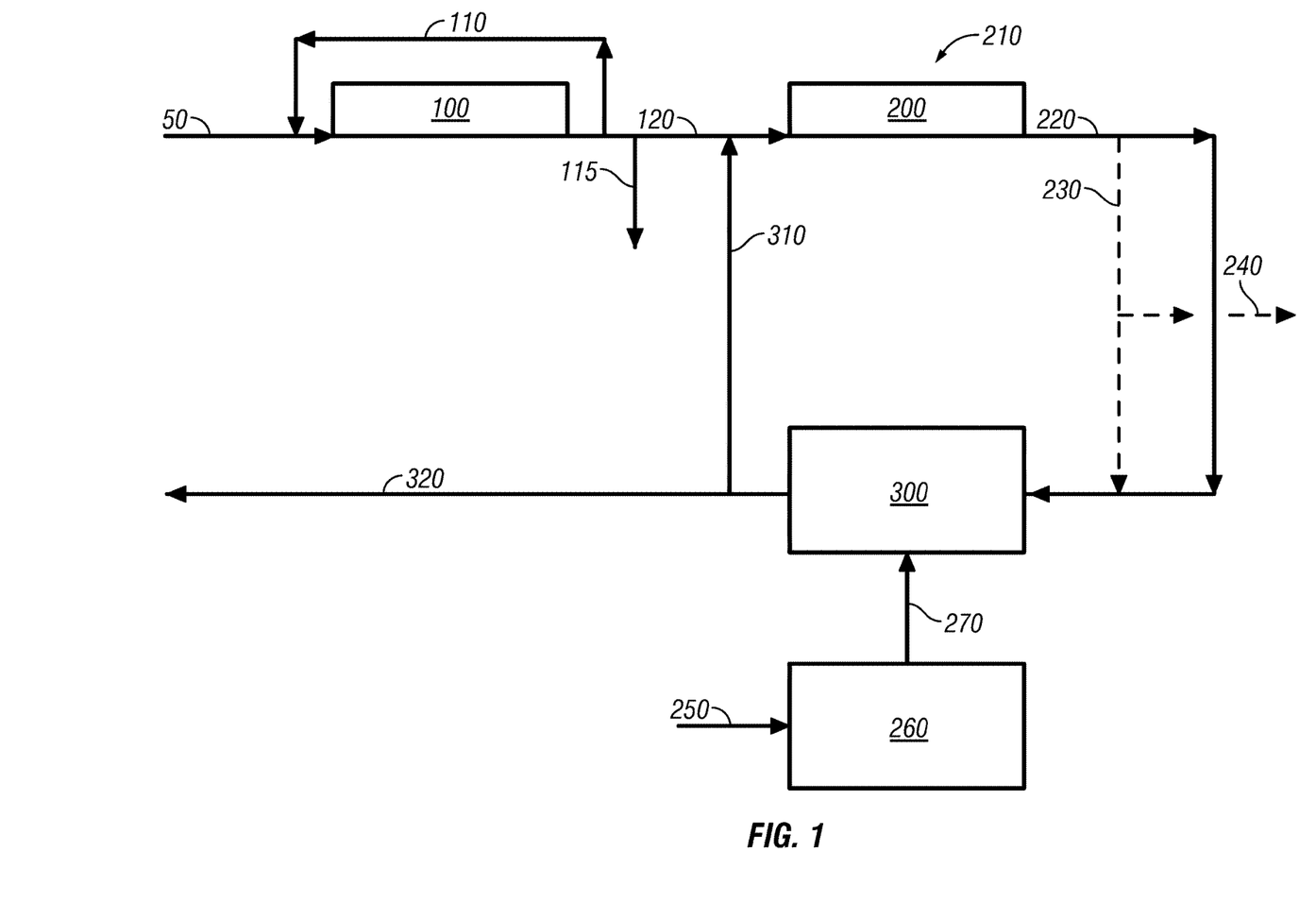
FIG. 1 provides a block flow diagram depicting the manufacture of methyl t-butyl ether from ethylene and methanol.

FIG. 1 provides a simplified block flow diagram of a process for manufacturing methyl t-butyl ether and other hydrocarbons, including higher molecular weight ethylene oligomers in accordance with the present disclosure, isomerized higher molecular weight ethylene oligomers, and higher-molecular-weight-ethylene-oligomer-based methyl ethers. The process as depicted involves two feedstocks: (1) ethylene and (2) methanol.

The depicted process excludes an optional first step of cracking the raw material. Instead, ethylene is introduced using a feed line (5) into a dimerization unit (100) with a suitable dimerization catalyst and under appropriate conditions. The dimerization unit produces n-butylenes. Any unconverted ethylene is recovered and recycled using a recycle line (110) through the dimerization unit.

Also, in some embodiments some ethylene units can undergo further dimerization to form higher molecular weight ethylene oligomers such as hexene and octene. Those higher molecular weight ethylene oligomers can be recovered or permitted to proceed through other steps in the process.

Next, the n-butylenes may be introduced using a feed line (120) into an isomerization unit (200) with a suitable isomerization catalyst and under appropriate conditions, or removed from the feed line (120) using an extraction line (115) for the collection of, e.g. high molecular weight ethylene oligomer (HMWEO). The isomerization unit produces isobutylene, which is removed from the unit via an extraction/feed line (220). Any unconverted n-butylene is recovered and recycled using a recycle line (210) through the isomerization unit (200).

Any higher molecular weight ethylene oligomers that were contained in the n-butylene stream can be isomerized to form isomerized higher molecular weight ethylene oligomers in the isomerization unit (200) and fed into a feed line (230). In turn, the isomerized higher molecular weight ethylene oligomers can be recovered from the process using a recovery line (240).

The depicted process further illustrates the optional fourth step of oxidizing methane to methanol via introduction of methanol using a feed line (260) into an etherification unit (300) further comprising a suitable etherification catalyst. Under appropriate conditions, the etherification unit produces a mixture of excess methanol and methyl t-butyl ether. The mixture can be distilled to give a methanol/methyl t-butyl ether azeotrope, and the MTBE may be collected.

Any higher molecular weight ethylene oligomers that were contained in the isobutylene stream can be introduced into an etherification unit (300) with methanol and a suitable etherification catalyst using the feed line (260). Under appropriate conditions, the etherification unit produces higher-molecular-weight-ethylene-oligomer-based methyl ether and the higher-molecular-weight-ethylene-oligomer-based methyl ether may be collected.

Figure 2:
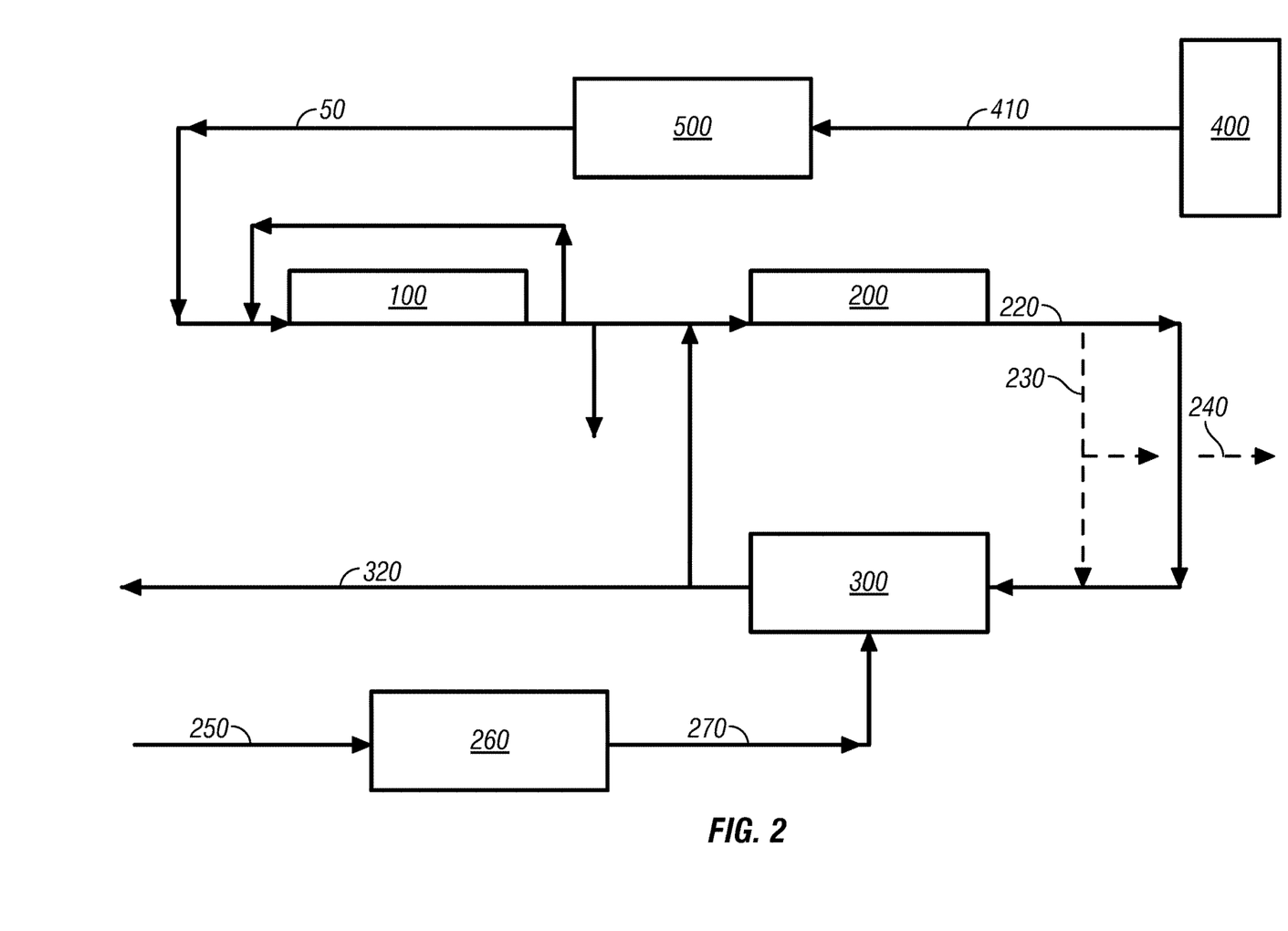
FIG. 2 provides an expanded block flow diagram depicting the manufacture of methyl t-butyl ether and other ethers from ethane and methane.

FIG. 2 provides an expanded, simplified block flow diagram of a process for manufacturing methyl t-butyl ether and other hydrocarbons in accordance with the present disclosure, including higher molecular weight ethylene oligomers, isomerized higher molecular weight ethylene oligomers, and higher-molecular-weight-ethylene-oligomer-based methyl ethers. The process as depicted involves two feedstocks: (1) ethane and (2) methane, which are respectively converted to ethylene and methanol.

The depicted process includes the optional first step of cracking the raw material. In this case, the raw material (i.e., feedstock) is ethane. The ethane is introduced into a steam cracker (500) using a feed line (410) operably connected to an ethane source (400). After the ethane is cracked, an ethylene-rich stream line (50) is produced. The ethylene-rich stream is introduced into the dimerization unit (100), and the process proceeds as described in FIG. 1.

As previously-noted, FIG. 2 depicts a process beginning with methane as a feedstock. The methane (i.e., natural gas) is introduced into an oxidixation processing unit (260) using a feed line (250), wherein the methane gas is first converted into a synthesis gas stream and then synthesized into methanol, according to the optional fourth step of oxidizing methane to methanol. The resulting methanol is introduced into the etherification unit (300).

In a general embodiment, the present disclosure provides for methyl t-butyl ether prepared by a process including (A) an optional first step including (i) cracking raw material made from or containing ethane and/or propane to form ethylene; and (ii) recovering residual uncracked raw material; (B) a second step including (i) dimerizing ethylene to form n-butylene; (C) a third step including (i) isomerizing the n-butylene to form isobutylene; (D) an optional fourth step including (i) oxidizing methane to form methanol; (E) a fifth step including (i) etherifying the isobutylene with methanol to form methyl t-butyl ether; and (F) a sixth step including (i) collecting methyl t-butyl ether.

In some embodiments, the present disclosure provides a method for preparing methyl t-butyl ether, gasoline alkylate, higher molecular weight ethylene oligomer, higher-molecular-weight-ethylene-oligomer-based methyl ether, isomerized higher molecular weight ethylene oligomer, or isomerized-higher-molecular-weight-ethylene-oligomer-based methyl ether.

EXAMPLES

The following examples are included to demonstrate embodiments. It should be appreciated by those of skill in the art that the techniques disclosed in the examples which follow represent techniques discovered to function in accordance with the present disclosure. However, those of skill in the art should, in light of the present disclosure, appreciate that many changes can be made in the specific embodiments which are disclosed and still obtain a like or similar result without departing from the spirit and scope of this disclosure.

Example I—Conversion of Ethylene and Methanol to MTBE

Ethylene is fed to a dimerization reactor comprising a catalyst (nickel dichloride tri-n-butyl phosphine) at a rate of 0.129 kg/min, and ethyl aluminium dichloride is further introduced at a rate of 0.098 kg/min. A solution of the catalyst in hexanes was used. The dimerization reactor was operated at a pressure of about 1586 kPa and a temperature of about 48 degrees Celsius.

The reaction mixture exited the reactor and was contacted with a 20% caustic solution, then washed with water.

The resulting dimerization mixture comprised the following components by weight percent based upon the total weight of the mixture: (a) 2-butylene—79.5 weight percent; (b) ethylene—7.0 weight percent; (c) 1-butylene—6.2 weight percent; (d) gasoline alkylate—7.2 weight percent; and (e) hexane—0.1 weight percent.

The washed dimerization mixture entered an ethylene fractionation column comprising 66 theoretical plates. The heavy fraction was transferred to an isomerization unit, and the ethylene fraction was recycled to the dimerization unit.

The isomerization unit operated at a pressure of about 250 kPa and a temperature of about 375 degrees Celsius. Based upon the total weight, the resulting isomerization mixture comprised the following products by weight percent: (a) isobutylene—40 weight percent; (b) 40% 2-butylene—40 weight percent; (c) 1-butylene—13 weight percent; (d) higher molecular weight olefins—6 weight percent; and (e) lighter hydrocarbons—1 weight percent.

The isomerization mixture was transferred to a "heavies" ($C_5^+$) fractionation column, which yielded 95% recovery of the higher molecular weight olefins. The higher molecular weight olefins were collected for use in gasoline products.

The lighter fraction of the isomerization mixture from the heavies fractionation column was transferred to an etherification unit. Methanol and water were added.

Based upon the total weight, the resulting etherification mixture comprised the following products by weight: (a) MTBE—49.9 weight percent; (b) 2-butylene—33.6 weight percent; (c) 1-butylene—11.4 weight percent; (d) methanol—2.8 weight percent; (e) isobutylene—1.3 weight percent; (f) light hydrocarbons—0.9 weight percent; and (g)

higher molecular weight olefins—0.1 weight percent. The etherification did not affect the amounts of 1-butylene, 2-butylene, light hydrocarbons, and higher molecular weight olefins.

The isobutylene had a 96% conversion to MTBE, with 0.4% selectivity for diisobutylene. The water was converted to tertiary butyl alcohol (t-butyl alcohol).

Example II—Preparation of Ethylene from Ethane

A feed consisting essentially of ethane, with less than about 10 weight percent of impurities such as propane, was cracked at a temperature of from about 815 degrees Celsius to about 870 degrees Celsius at a pressure of from about 100 kPa to about 170 kPa. The cracked product was cooled and then subjected to oil quenching, followed by water quenching to a temperature of about 38 degrees Celsius at about 70 kPa, after which it was subjected to compression to a pressure of about 3600 kPa. The compressed stream was cooled to about 16 degrees Celsius, dried, and then chilled and partially condensed in stages to a temperature of at least about −151 degrees Celsius to separate a high purity hydrogen stream from the compressed stream. Methane was then separated from the remaining hydrocarbons via distillation as an overhead product from a demethanation tower.

The cracked product from the bottoms of the demethanizer was passed to the distillation tower which operates at a bottom temperature of about 77 degrees Celsius and at a pressure of about 2400 kPa to form an overhead stream that consists essentially of ethane and ethylene and a bottoms stream that contains $C_3$ and heavier hydrocarbons.

The overhead stream was selectively hydrogenated using similar conditions and catalyst, followed by distillation of the hydrogenated stream in a tower with a bottom temperature of about −6 degrees Celsius and pressure of about 1930 kPa to remove a stream consisting essentially of ethane, resulting in a separate stream consisting essentially of ethylene.

Example III—Preparation of Butylenes from Ethylene

An ethylene stream was passed to an ethylene dimerization reactor operating at a temperature of about 38 degrees Celsius, a pressure of about 1030 kPa, and a residence time of about 30 minutes, using a mixture of ethyl aluminum dichloride and a nickel salt-phosphine complex to catalyze the reaction. After quenching the reaction and removing the residual catalyst, the dimerized product was subjected to fractional distillation at a bottom temperature of about 110 degrees Celsius and 480 kPa to remove $C_5$ and heavier hydrocarbons as an automotive gasoline product and to produce a butylene-rich stream. The butylene-rich stream was dried at ambient temperature and a pressure of about 414 kPa using a molecular sieve adsorbent.

Example IV—Temperature Effects on Dimerization of Ethylene

A dimerization unit was operated at a fixed pressure of about 1165 kPa, a residence time of about 30 minutes, and a catalyst (comprising a nickel salt-phosphine complex with ethyl aluminium dichloride) concentration of about 70 ppm. When the temperature was increased from about 34 degrees Celsius to about 43 degrees Celsius, the ethylene conversion rate increased from about 92% to about 95%. However, the selectivity decreased from about 94.5% to about 92%.

Example V—Catalyst Concentration Effects on Dimerization of Ethylene

A dimerization unit was operated at a fixed pressure of about 1103 kPa, a residence time of about 15 minutes, and a temperature of about 43 degrees Celsius. When the catalyst (comprising a nickel salt-phosphine complex with ethyl aluminium dichloride) composition was increased from about 5 ppm to about 30 ppm, the ethylene conversion rate increased from about 97.5% to about 99.3%.

Example VI—Temperature Effects on Dimerization of Ethylene (at Lower Pressure)

A dimerization unit was operated at a fixed pressure of about 483 kPa, a residence time of 20 minutes, and a catalyst (comprising a nickel salt-phosphine complex with ethyl aluminium dichloride) concentration of about 10 ppm. When the temperature was decreased from about 52 degrees Celsius to about 43 degrees Celsius, the butene selectivity increased from about 81.5% to about 87.2%.

Example VII—Isomerization of N-Butylenes to Isobutylene (Low WHSV)

The reactor was first loaded with an inert packing material in the preheating zone. The inert packing materials used were either a small mesh corundum or a bed of inert clay catalyst support balls. The inert bed depth varied depending on the thermocouple points the catalyst was to occupy. A typical loading depth was about 75 centimeters of inert material.

Above the packing material, a weighed amount of catalyst was added to coincide with thermocouple points for reading the temperature during the experiment.

The amount of catalyst used varied depending on the weight hourly space velocity (WHSV) desired and the flow rates attainable with the equipment. A typical loading consisted of about 97 grams of catalyst, which corresponded to a loading of about 10 centimeters in the reactor.

Above the catalyst, another layer of packing material was added to form a distinct zone of catalyst.

The feed stream used comprised about 30-50 weight percent butene-2, about 25-45 weight percent butene-1, and about 20-30 weight percent n-butane, with all weight percents based on the total weight of the feed stream.

Testing began by warming up the reactor to a minimum operating temperature, usually greater than 200 degrees Celsius. The warming step was performed under a nitrogen purge at a pressure of about 100 kPa to about 340 kPa.

Once the reactor was warmed, the flow control valve was opened to introduce feed to the reactor, and the nitrogen purge was turned off. The weight hourly space velocities varied from about 1 to about 30. The operating temperatures used varied in a range from about 200 degrees Celsius to about 550 degrees Celsius. The pressures varied in response to restriction from the catalyst and reactor. Most of the testing was performed with the pressure control valve open to the atmosphere. The recorded values of the effluent pressure, however, were in a range of about 100 kPa to about 310 kPa.

Samples of the reactor effluent were manually sampled using the sampling system and gas chromatography. The analysis was performed with a boiling point separation column or an alumina column.

The catalyst was hydrogen ferrierite that was charged at about 400 grams. The pressure was about 103 kPa to about 117 kPa, and the weight hourly space velocity was about 2.

All concentrations are shown in weight percent, based upon the total weight of the sample, and all temperatures are shown in degrees Celsius. The measurements were taken at the times shown in Table I (e.g., 1 hour, 5.6 hours, 16 hours, or 36 hours).

TABLE I

| | | Measurement Time | | | |
|---|---|---|---|---|---|
| | | 1 hour | 5.6 hours | 16 hours | 36 hours |
| | | Inlet Temperature | | | |
| | | 370 | 295 | 255 | 319 |
| Components | Initial Concentration | Measurement Concentration | | | |
| Methane | 0.00 | 0.08 | 0.00 | 0.00 | 0.00 |
| Ethane | 0.01 | 0.13 | 0.01 | 0.01 | 0.01 |
| Ethylene | 1.17 | 0.20 | 0.17 | 0.33 | 0.25 |
| Propane | 0.00 | 3.14 | 0.08 | 0.03 | 0.10 |
| Propylene | 0.15 | 2.02 | 0.69 | 0.52 | 0.95 |
| Isobutane | 0.01 | 1.18 | 0.17 | 0.06 | 0.17 |
| n-butane | 0.09 | 4.97 | 1.50 | 1.11 | 1.54 |
| cis 2-butene | 29.45 | 2.38 | 7.45 | 14.21 | 7.17 |
| trans 2-butene | 57.67 | 3.46 | 10.95 | 20.17 | 10.43 |
| 1-butene | 11.37 | 1.45 | 3.56 | 7.84 | 4.52 |
| isobutylene | 0.02 | 7.69 | 16.10 | 12.57 | 19.50 |
| 1,3-butadiene | 0.01 | 0.00 | 0.00 | 0.00 | 0.00 |
| Heavies (C5+) | 0.05 | 73.30 | 59.32 | 43.15 | 55.36 |

Example VIII—Isomerization of N-Butylenes to Isobutylene (Higher WHSV)

Example VIII was performed according to the procedure described in Example VII except that the catalyst was hydrogen ferrierite that was charged at about 96 grams. The pressure was about 103 kPa to about 117 kPa, and the weight hourly space velocity was about 15.

All concentrations are shown in weight percent, based upon the total weight of the sample, and all temperatures are shown in degrees Celsius. The measurements were taken at the times shown in Table II (e.g., 2 hours, 12 hours, 24 hours, 31 hours, or 39 hours).

TABLE II

| | | Measurement Time | | | | |
|---|---|---|---|---|---|---|
| | | 2 hour | 12 hours | 24 hours | 31 hours | 39 hours |
| | | Inlet Temperature | | | | |
| | | 251 | 319 | 371 | 372 | 371 |
| Components | Initial Conc. | Measurement Concentration | | | | |
| Methane | 0.00 | 0.00 | 0.01 | 0.00 | 0.00 | 0.00 |
| Ethane | 0.01 | 0.01 | 0.02 | 0.01 | 0.01 | 0.01 |
| Ethylene | 1.17 | 0.60 | 0.72 | 0.55 | 0.80 | 0.84 |
| Propane | 0.00 | 0.04 | 0.09 | 0.03 | 0.02 | 0.01 |
| Propylene | 0.15 | 0.19 | 1.25 | 0.81 | 0.70 | 0.57 |
| Isobutane | 0.01 | 0.02 | 0.12 | 0.06 | 0.03 | 0.02 |
| n-butane | 0.09 | 0.47 | 1.22 | 0.86 | 0.72 | 0.55 |
| Methyl cyclopropane | 0.00 | 0.00 | 0.00 | 0.01 | 0.04 | 0.02 |
| cis 2-butene | 29.45 | 26.20 | 14.67 | 18.23 | 20.15 | 23.48 |
| trans 2-butene | 57.67 | 40.93 | 20.76 | 26.05 | 28.33 | 32.28 |
| 1-butene | 11.37 | 17.60 | 9.59 | 13.95 | 14.14 | 16.47 |
| isobutylene | 0.02 | 2.65 | 23.53 | 31.89 | 26.97 | 21.72 |
| 1,3-butadiene | 0.01 | 0.00 | 0.00 | 0.00 | 0.00 | 0.00 |
| Heavies ($C_5^+$) | 0.05 | 11.29 | 28.02 | 7.55 | 8.09 | 4.03 |

It should be understood that various changes, substitutions and alterations can be made herein without departing from the spirit and scope of this disclosure as defined by the appended claims. Moreover, the scope of the present application is not intended to be limited to the particular embodiments of the process, machines, manufacture, compositions of matter, means, methods and steps described in the specification. As one of the ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein can be utilized. Accordingly, the appended claims are intended to include within their scope such processes, machines, manufacture, compositions of matter, means, methods, or steps.

What is claimed is:

1. A process for manufacturing methyl t-butyl ether (MTBE) comprising:
   a first step comprising cracking raw material comprising ethane or propane to form ethylene; and recovering residual uncracked raw material;
   a second step comprising dimerizing ethylene to form a n-butylene feed stream, wherein the n-butylene feed stream comprises:
   (i) about 30 to 50 wt. % of 2-butene, based on the total weight of the feed stream,
   (ii) about 25 to 45 wt. % of 1-butene, based on the total weight of the feed stream, and
   (iii) a higher molecular weight ethylene oligomer
   wherein the dimerizing step is performed at a temperature of about 10-100° C., wherein the dimerizing step takes place in the presence of a dimerization catalyst, wherein the dimerization catalyst comprises a nickel compound and an aluminum compound, and wherein the catalyst has a Ni:Al ratio from 0.9:10 to 1:2.5;
   a third step comprising isomerizing the n-butylene feed stream to form an isobutylene stream using a isomerization catalyst at a weight hourly space velocity (WHSV) of 0.2-4 kg feedstock per kg catalyst per hour at a pressure of about 345-3450 kPa and a temperature of about 40-200° C., wherein the isomerization catalyst is an acidic isomerization catalyst;

recovering unconverted n-butylene;

alkylating isobutylene with isobutane at a pressure of at least 600 kPa to form gasoline alkylate;

recovering gasoline alkylate;

isomerizing the higher molecular weight ethylene oligomer; and recovering the isomerized higher molecular weight ethylene oligomer;

a fourth step comprising oxidizing methane to form methanol;

a fifth step comprising etherifying the isobutylene stream with methanol to form methyl t-butyl ether;

etherifying the higher molecular weight ethylene oligomer contained in the isobutylene stream with methanol to form a higher-molecular-weight-ethylene-oligomer-based methyl ether;

recovering the higher-molecular-weight-ethylene-oligomer-based methyl ether;

etherifying an isomerized higher molecular weight ethylene oligomer contained in the isobutylene stream with methanol to form an isomerized-higher-molecular-weight-ethylene-oligomer-based methyl ether; and recovering the isomerized-higher-molecular-weight-ethylene-oligomer-based methyl ether; and a sixth step comprising collecting the methyl t-butyl ether.

2. The process of claim 1, wherein the second step further comprises:

recovering unconverted ethylene;

alkylating n-butylene with isobutane to form gasoline alkylate; and recovering the gasoline alkylate.

3. The process of claim 1, wherein the second step further comprises:

recovering unconverted ethylene;

dimerizing combinations of at least three ethylene molecules to form a higher molecular weight ethylene oligomer; and recovering the higher molecular weight ethylene oligomer.

4. The process of claim 3, wherein the alkylating step is performed at a catalyst:hydrocarbon volume ratio of 1:1 to 4:1.

5. The process of claim 1, wherein the weight hourly space velocity (WHSV) ranges from about 1 to about 3 kg feedstock per kg catalyst per hour.

6. The process of claim 1, wherein the n-butylene feed stream is contacted with a caustic solution.

7. The process of claim 6, wherein the caustic solution is a 20% caustic solution.

8. The process of claim 1, wherein the fourth step further comprises:

recovering unconverted methane.

9. The process of claim 1, wherein the cracking step further comprises processing of a cracked product containing hydrogen, ethylene, propylene, a hydrocarbon or pyrolysis gasoline.

* * * * *